US00PP14731P3

(12) United States Plant Patent
Twomey et al.

(10) Patent No.: US PP14,731 P3
(45) Date of Patent: Apr. 27, 2004

(54) HYBRID TEA ROSE PLANT NAMED 'BAIPEACE'

(50) Latin Name: *Rosa hybrida*
Varietal Denomination: BAIpeace

(75) Inventors: Jerry Twomey, Leucadia, CA (US); Peter P. Lim, Yamhill, OR (US)

(73) Assignee: Bailey Nurseries, Inc., St. Paul, MN (US)

( * ) Notice: Subject to any disclaimer, the term of this patent is extended or adjusted under 35 U.S.C. 154(b) by 200 days.

(21) Appl. No.: 10/131,073

(22) Filed: Apr. 25, 2002

(65) Prior Publication Data

US 2003/0005493 P1 Jan. 2, 2003

(30) Foreign Application Priority Data

May 2, 2001 (FR) ..... 17728

(51) Int. Cl.[7] ..... A01H 5/00
(52) U.S. Cl. ..... Plt./131
(58) Field of Search ..... Plt./131

*Primary Examiner*—Bruce R. Campell
*Assistant Examiner*—Annette H. Para
(74) *Attorney, Agent, or Firm*—Burns, Doane, Swecker & Mathis, L.L.P.

(57) ABSTRACT

A new and distinct variety of Hybrid Tea rose plant is provided which abundantly forms on a recurrent basis fully double blossoms that display a high center and an attractive blend of yellow and carmine pink coloration. The blossoms also display a sweet fruity fragrance. The plant exhibits a vigorous compact and upright growth habit, glossy dark green foliage, and good tolerance to Blackspot, Powdery Mildew, and Rust. The attractive dark green foliage contrasts nicely with the bicolored blossom coloration. The new variety is particularly well suited for growing as attractive ornamentation in parks and gardens.

3 Drawing Sheets

SUMMARY OF THE INVENTION

The new variety of *Rosa hybrida* Hybrid Tea rose plant was created at Yamhill, Oreg. during 1991 by artificial pollination wherein two parents were crossed which previously had been studied in the hope that they would contribute the desired characteristics. The female parent (i.e., the seed parent) was an unnamed seedling (non-patented in the United States) from the breeding program. The male parent (i.e., the pollen parent) was the 'Peace' variety (U.S. Plant Pat. No. 591). The parentage of the new variety can be summarized as follows:

Unnamed Seedling×'Peace'.

The seeds resulting from the above pollination were sown and plants were obtained which were physically and biologically different from each other. Selective study resulted in the identification during 1993 of a single plant of the new variety having the distinctive ornamental characteristics hereafter described.

It was found that the new variety of the present invention:

(a) exhibits a vigorous compact and upright growth habit, (b) abundantly forms on a continuous basis attractive fully double blossoms that display a high center and a blend of yellow and carmine pink coloration, (c) forms dense glossy dark green foliage that contrasts well with the blossom coloration, and (d) is particularly well suited for growing as attractive ornamentation in parks and gardens.

The disease tolerance is good with respect to Blackspot, Powdery Mildew, and Rust.

The new variety well meets the needs of the horticultural industry and can be grown to advantage in the landscape where attractive ornamentation is desired. The distinctive blossoms are displayed throughout the summer. The plant can be grown as a specimen or as a mass planting.

The new variety can be readily distinguished from other varieties including its ancestors. For instance, the blossoms commonly exhibit a deeper pink coloration than the 'Peace' variety and darker green foliage than the 'Peace' variety.

The new variety has been found to undergo asexual propagation by budding on an understock. Asexual propagation by this technique at Yamhill, Oreg., and at Phoenix, Ariz. has shown that the characteristics of the new variety are stable and are strictly transmissible by such asexual propagation from one generation to another.

Initially the new plant was designated 91G55-1B. The new variety subsequently has been named the 'BAIpeace' variety, and is being promoted while using the LOVE & PEACE trademark. The new variety also has been named an All-American Rose Selections winner for the year 2002.

BRIEF DESCRIPTION OF THE PHOTOGRAPHS

The accompanying photographs show as nearly true as it is reasonably possible to make the same in a color illustrations of this character, typical specimens of the new variety. The rose plants of the new variety had been propagated by budding, were approximately two years of age, and were being grown outdoors on Rosa 'Dr. Huey' understock.

FIG. 1 illustrates typical blossoms and foliage of the new variety while growing in a garden setting at St. Paul, Minn. during July. The blossoms in the foreground were in the final stages of opening and display the coloration blend of golden yellow irregularly edged with carmine pink. The attractive dense glossy dark green foliage additionally is shown.

FIG. 2 illustrates a typical single bud of the new variety in the early stages of opening while growing during July at St. Paul, Minn. The sepals bearing numerous extensions and glossy dark green foliage also are shown.

DETAILED DESCRIPTION

Figure 1:
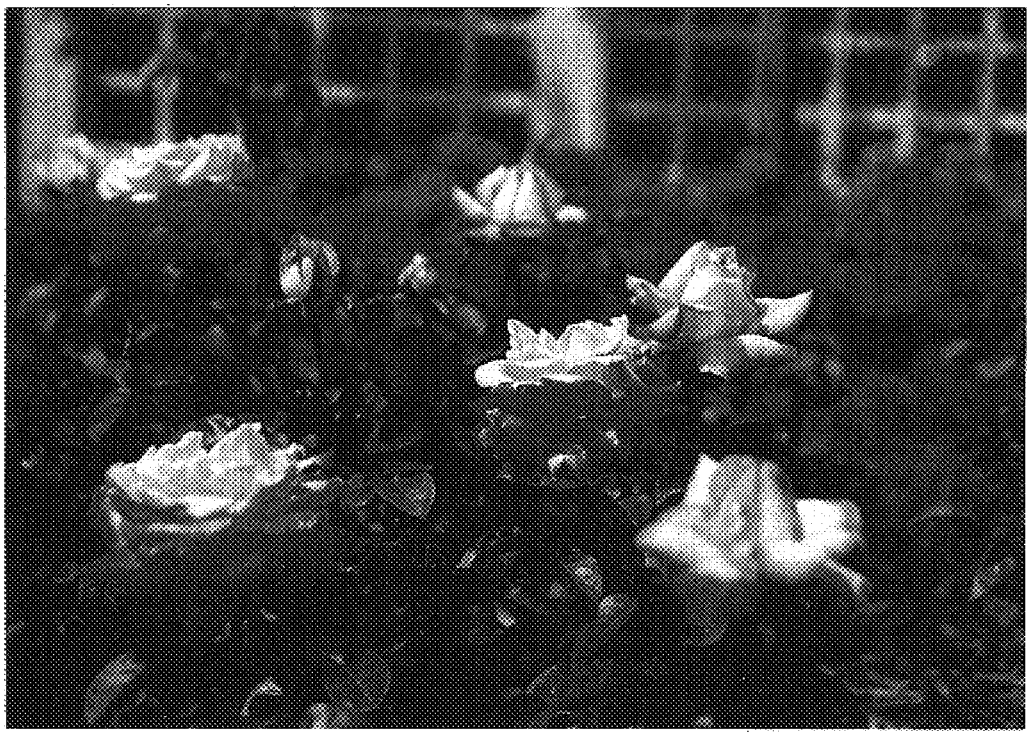
Figure 2:
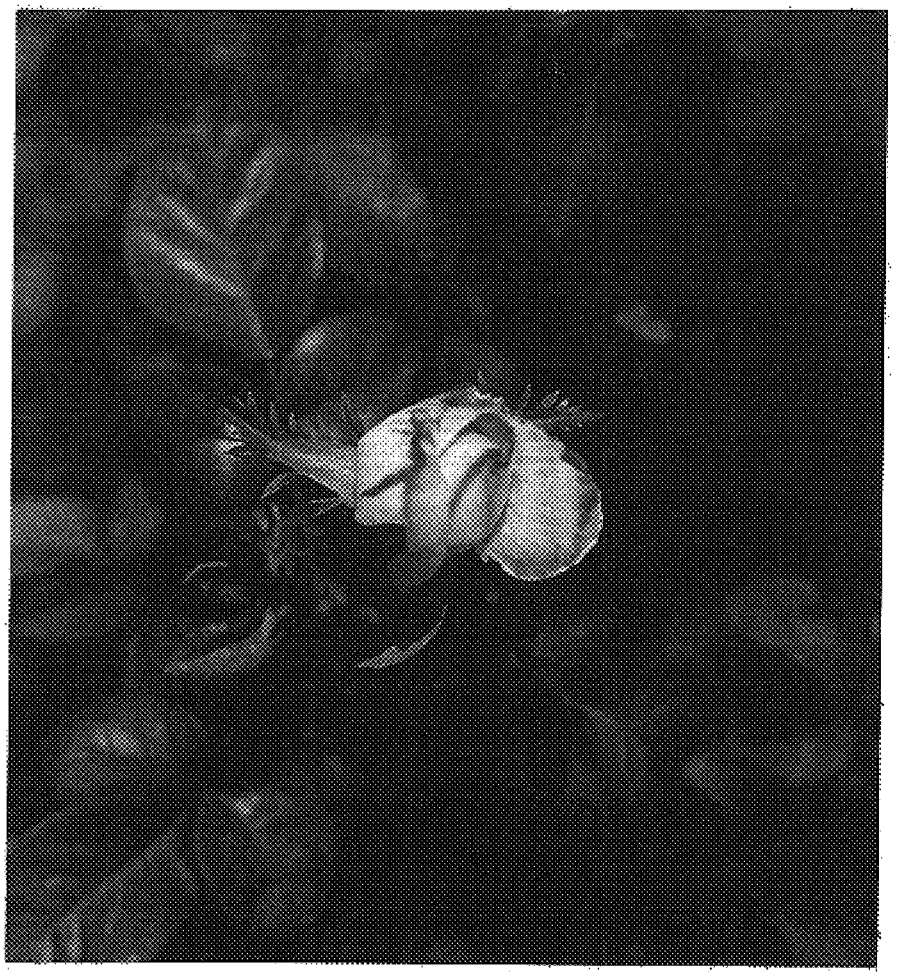
Figure 3:
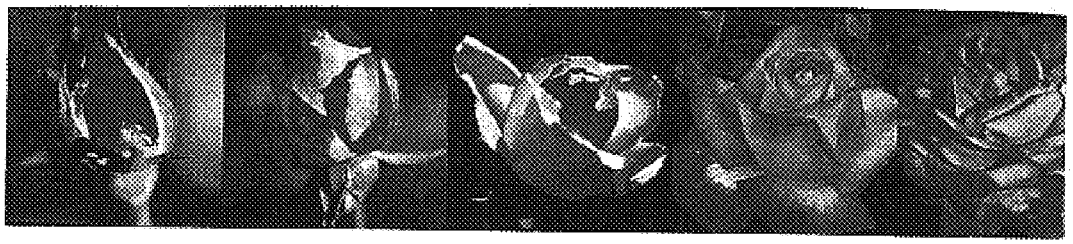
FIG. 3 illustrates from left to right typical flowers of the new variety in progressive stages of opening beginning with the bud stage. The plant was being grown during the summer while undergoing testing at Portland, Oreg.
Figure 4:
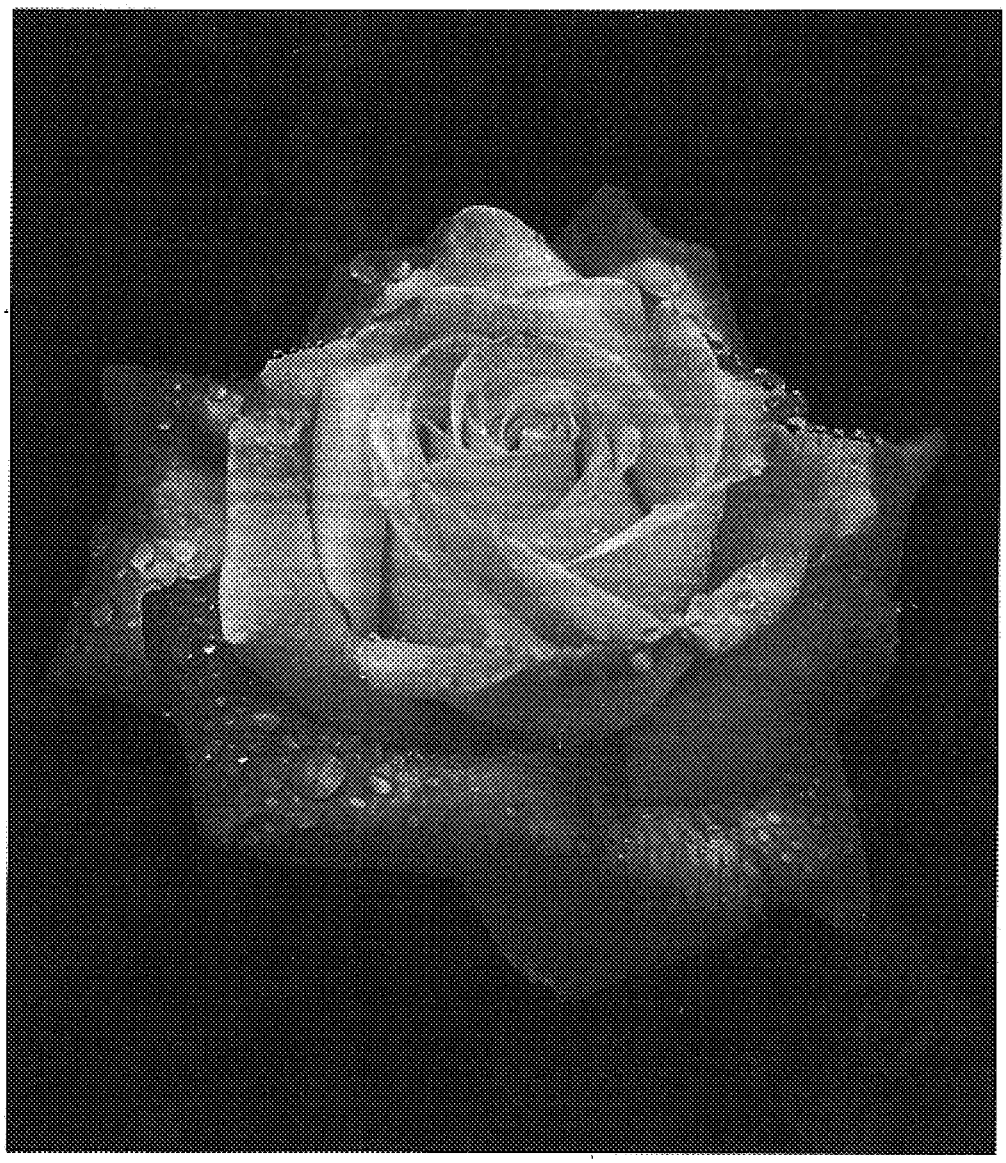
FIG. 4 illustrates a typical open bloom of the new variety wherein the blend of golden yellow and carmine pink coloration is well illustrated. The plant was being grown during the summer while undergoing testing at Portland, Oreg.

The chart used in the identification of the colors is that of The Royal Horticultural Society (R.H.S. Colour Chart). Common color terms are to be accorded their ordinary dictionary significance. The description is based on the observation of two year-old plants while budded on Rosa 'Dr. Huey' understock and growing outdoors during June and July at St. Paul, Minn. and during October at Phoenix, Ariz.

Botanical classification: *Rosa hybrida*, var. 'BAIpeace'.
Class: Hybrid Tea.
Plant:
- *Height.*—Approximately 1 to 1.5 m on average at the end of the growing season.
- *Width.*—Approximately 90 cm on average at the end of the growing season.
- *Stem length.*—Commonly approximately 30 to 80 cm, and approximately 60 cm on average.
- *Habit.*—Compact and upright.

Branches:
- *Color.*—Young stems: near Yellow-Green Group 144B with some highlights of Red-Purple Group 59A. Adult wood: near Yellow-Green Group 144B suffused with Red-Purple Group 59A.
- *Thorns.*—Size: commonly approximately 0.6 to 1.5 cm in length on average with some smaller bristles/prickles near the peduncle. Quantity: moderate. Color: near Red-Purple Group 59B. Configuration: curved downwards on the upper surface and concave under surface.

Leaves:
- *Stipules.*—Generally parallel with the auricle facing outward.
- *Petioles.*—Upper surface: Green Group 139C with highlights of Red-Purple Group 59A. Under surface: Yellow-Green Group 144B.
- *Leaflets.*—Number: 3, 5 (most often), and 7. Shape: ovate with a rounded base and an acuminate tip. Serration: finely serrate. Texture: leathery. General appearance: dark green with a glossy surface. Color (young foliage): Upper surface: Red-Purple Group 59A with highlights of Green Group 138B. Under surface: near Red-Purple Group 59B. Color (adult foliage): Upper surface: commonly Green Group 137A to Green Group 139A. Under surface: Green Group 138A with some presence of Red-Purple Group 59C. Main vein: Green Group 138A.

Inflorescence:
- *Number of flowers.*—Commonly one per stem.
- *Peduncle.*—With some prickles, near Green Group 139C in coloration, and the length is approximately 4.5 cm on average.
- *Sepals.*—Upper surface: Green Group 137D to Green Group 139C in coloration. Under surface: near Yellow-Green Group 139C with areas of Red-Purple Group 59C, and some pubescence. Size: approximately 3 cm in length with some extensions.
- *Buds.*—Shape: pointed. Size: medium to large. Length: approximately 2.5 to 3 cm on average. Diameter: approximately 1.5 to 2 cm. Color: Upper surface: Yellow-Green Group 154B with highlights of Red-Purple Group 61C. Under surface: Yellow Group 11A and Yellow Group 12C with highlights of Red-Purple Group 60B.
- *Flower.*—Shape: fully double, high-centered spiral tea. Diameter: approximately 13 cm on average. Height: approximately 3 to 4.5 cm. Color (when blooming): Upper surface: Yellow Group 12A at the base fading to Yellow Group 11C and blended with Red-Purple Group 63A to 63C particularly towards the margins. Under surface: Yellow Group 13C fading to Yellow Group 12D blended with highlights of Red-Purple Group 63C to 63D particularly towards the margins. The display of bicolor on both surfaces often is irregular in its presentation. Fading on both surfaces appears to be accelerated by extreme heat. Fragrance: sweet fruity. Lasting quality: the blossoms commonly last approximately 4 to 6 days from bud on the plant on average depending upon the temperature, and approximately 5 to 7 days when cut and placed in a vase at the opening bud stage. Petal number: approximately 40 on average under normal growing conditions. Petal shape: wedge-shaped commonly with a curled apex when fully open. Petal texture: satiny. Petal drop: commonly the petals do not detach at full blossom maturity. Stamen number: approximately 78 on average. Anthers: near Yellow-Orange Group 14A in coloration. Pollen: present and yellow in coloration. Filament number: commonly approximately 121 on average. Filaments: near Yellow Group 9A in coloration. Pistils: approximately 102 on average. Stigmas: near Yellow Group 14B in coloration. Styles: Yellow-Green Group 154B in coloration. Receptacle: substantially round, and separate and free with achenes at the bottom and the wall. Hips: round/ovoid in configuration. Seeds: kernel-shaped, hard, brown in coloration, and rugose at the apex.

Development:
- *Vegetation.*—Vigorous, strong, and tough.
- *Blooming.*—Abundant and continuous.
- *Resistance to diseases.*—Highly tolerant to Blackspot, Rust, and Powdery Mildew.
- *Aptitude to bear fruit.*—Good. However, hips are not readily formed in Minnesota due to the shorter growing season and frequent deadheading.
- *Hardiness zone.*—Zone 6. Appropriate winter protection is recommended in colder climates.

We claim:

1. A new and distinct variety of Hybrid Tea rose plant characterized by the following combination of characteristics:

(a) exhibits a vigorous compact and upright growth habit, (b) abundantly forms on a continuous basis attractive fully double blossoms that display a high center and a blend of yellow and carmine pink coloration, (c) forms dense glossy dark green foliage that contrasts well with the blossom coloration, and (d) is particularly well suited for growing as attractive ornamentation in parks and gardens;

substantially as herein shown and described.

* * * * *